United States Patent
Underwood et al.

(10) Patent No.: US 6,738,135 B1
(45) Date of Patent: May 18, 2004

(54) SYSTEM FOR INSPECTING EUV LITHOGRAPHY MASKS

(76) Inventors: James H. Underwood, 6680 Alhambra Ave., Martinez, CA (US) 94553;
Rupert C. C. Perera, 6680 Alhambra Ave., Martinez, CA (US) 94553;
Patrick Naulleau, 6680 Alhambra Ave., Martinez, CA (US) 94553

( * ) Notice: Subject to any disclaimer, the term of this patent is extended or adjusted under 35 U.S.C. 154(b) by 0 days.

(21) Appl. No.: 10/153,135

(22) Filed: May 20, 2002

(51) Int. Cl.[7] .............................................. G01N 21/88
(52) U.S. Cl. .................................................... 356/237.5
(58) Field of Search ........................... 356/237.1–237.5, 356/445; 430/5, 311; 250/492.1, 492.2

(56) References Cited

U.S. PATENT DOCUMENTS

| | | | |
|---|---|---|---|
| 5,541,416 A | * | 7/1996 | Washizuka ............... 250/458.1 |
| 5,940,173 A | * | 8/1999 | Tomii et al. ................. 356/445 |
| 6,555,828 B1 | * | 4/2003 | Bokor et al. .............. 250/492.2 |
| 2003/0043370 A1 | * | 3/2003 | Goldberg ................. 356/237.5 |
| 2003/0067598 A1 | * | 4/2003 | Tomie ...................... 356/237.2 |

* cited by examiner

*Primary Examiner*—Hoa Q. Pham
(74) *Attorney, Agent, or Firm*—Theodore J. Bielen, Jr.

(57) ABSTRACT

A system for inspecting lithography masks utilizing a laser source to produce a coherent electromagnetic radiation pulse. The pulse is passed to a target which creates a plasma resulting in an extreme ultraviolet (EUV) beam. The beam is condensed and passed through an aperture to define a cross-sectional area of the condensed EUV beam on a lithography mask. A transmission zone plate resolves the image reflected from the lithography mask and passes the image to a detector for analysis.

10 Claims, 1 Drawing Sheet

SYSTEM FOR INSPECTING EUV LITHOGRAPHY MASKS

BACKGROUND OF THE INVENTION

The present invention relates to a novel system for inspecting lithography masks. Optical lithography is currently used to produce electronic chips in the semiconductor industry.

Masks used in the Extreme Ultraviolet (EUV) lithographic process in the production of electronic chips employs a "reflection mask". A mask blank is first prepared by coating a suitable substrate, such as a silicon wafer, with a multi layer reflector. The mask blank is then patterned by an appropriate process e.g., electron beam writing, to produce a finished mask used in the lithographic process. The pattern on the mask represents an enlarged version of the microcircuit that is to be fabricated using such mask.

Optical lithography techniques are presently used to illuminate masks in order to produce a semi conductor chip. Currently, optical lithography operates in the 130 nm node (plateau). It has been hypothecated that optical lithography may produce semiconductor chips at a lower node i.e. 100 nm, although it is not certain this can occur. It is known that smaller and smaller capability plateaus will result in chips which may be employed in faster circuits, result in denser memories, and eventually higher capacity computers.

It has been proposed that extreme ultraviolet radiation (EUV) be used in substitution for light used in optical lithography. In other words, extreme ultraviolet lithography (EUVL) employs the short wavelength illumination of the EUV radiation (10–14 nm). Recent advances in EUVL has successfully performed the lithography process employing a stepper device operating in a vacuum and using reflective optics.

The mask used for the EUVL process, however, must be free of defects. Since the features on the semi-conductor chips produced by the EUVL process are in the order of a fraction of a micrometer, any particles or in perfections on the mask on the active area of the pattern can be transferred to the pattern circuit. Such defects will cause the circuit to be improperly written and, thus, malfunction. Consequently, it is necessary to inspect the mask blanks in the EUVL process for defects before they are patterned, and to inspect the mass after patterning to make sure that no defects have been created in the pattern area by this process.

Defects generally fall into two categories, amplitude defects, and phase defects. Amplitude defects are caused by particles or other contaminants which lie on the patterned mask and absorb EUV radiation. Amplitude defects create spurious "dark spots" on a demagnified image of the pattern. Amplitude defects may also occur by particles underlying a multilayer coating, which is typical in semiconductor chip production.

Phase defects are caused by defects in the mask structure and introduce an optical path difference when the EUV light is directed to the mask. The result is a non-faithful or distorted image of the projected image on the corresponding point of the wafer.

Optical lithography is also concerned with defect-free mask blanks. However, in the case EUVL, the size of the defects on a mask blank which affects the production of a semi-conductor chip is much smaller than those of importance in optical lithography. Since the EUVL tool writes features of 0.1 micrometers and smaller, defects of 50 nanometers in size and smaller will be of significant importance.

In the past, optical systems have been developed which have allowed the detection and approximate location of small defects by sensing the scattering of light by such defects. Such instruments are effective for screening mask blanks and rejecting those with a successive number of defects. However, these systems are not applicable to patterned masks since the scattered signal from the pattern overwhelms the signal from a defect. Direct optical microscopes are of little or no use since both the features of the pattern and the defects are below the resolution limit of an optical microscope.

In the past, reflecting soft X-ray microscopes have been produced to observe the microscopy of biological and semiconductor elements. However, these systems require optics to concentrate the soft X-ray beam and are non-specific as to examination of a certain area of a surface being analyzed. Reference is made to U.S. Pat. No. 5,177,774 which describes a soft X-ray system of this type.

A system which inspects defects in EUV lithography masks would be a notable advance in the electronics field.

BRIEF SUMMARY OF THE INVENTION

In accordance wit the present invention a novel and useful system for inspecting defects in EUV lithography masks is herein provided.

The mask of the present invention employs a laser plasma source which is produced by a Q-switched pulsed laser. Such a laser produces a pulsed coherent electromagnetic beam that impinges on a metallic target such as one composed of gold, copper, or the like creating an EUV beam. The EUV beam is essentially continuous and possesses a wavelength that ranges between 10 and 16 nanometers. Typically a bandwidth is selected which generally coincides with the narrow wavelength band around the wavelength of operation for manufacturing chips using the EUV mask.

After production of the EUV beam, the "light" is delivered to a EUV mask by a focusing or condensing means. Such means may take the form of a multimirror, multilayer-coated condenser known as a Schwarzschild system. The collection angle of the Schwarzschild system is designed to match the collection angle of the stepper condenser employed to produce the semi-conductor chip. An aperture plate is employed to define the cross-sectional area of the condensed EUV beam for impingement on and reflection from the lithography mask. The image of illumination is as small as 20 by 20 micro meters area of the mask. Fiducial-based location or mask positioning is accomplished with conventional transfer systems used to move mask blanks from a standard container to the inspection area for use with the system of the present invention.

The image of the small area illuminated on the mask blank is reflected from the mask and passed to a transmission zone plate. The transmission zone plate collects and resolves an image of the EUV reflected from the lithography mask. The beam is passed to a detector for receiving the EUV beam and producing an aerial image of the mark. The image may be displayed on a charge coupled device camera (CCD camera). The image is then analyzed for defects within the observational field of view for both patterned and unpatterned fields. The effective aerial image pixel size is approximately 20 nanometers. An image is found on the detector in less than one second of CCD integration based on the EUV flux from the laser plasma source producing the EUV beam.

It may be apparent that a novel and useful system for inspecting EUV lithography masks has been hereinabove described.

It is therefore an object of the present invention to provide a system for inspecting EUV lithography masks which is capable of assessing the severity of a defect utilizing high-speed scanning tools directly observing the aerial image, which is the same as that presented to the wafer in an actual stepper apparatus.

Another object of the present invention is to provide a system for inspecting EUV lithography masks that are capable of alignment of the mask blank fiducials and is capable of employing a semi-automatic fiducial mark detection system to locate the effected area on a EUV mask or reticle.

Yet another object of the present invention is to provide a system for inspecting a EUV lithography mask which is capable of inspecting unpatterned and patterned EUV reticles.

Another object of the present invention is to provide a system for inspecting EUV lithography masks that utilizes a compact laser produced plasma EUV source and also provides for EUV optics.

Yet another object of the present invention is to provide a system for inspecting an EUV lithography mask under illumination conditions which match EUVL stepper conditions in the manufacturing of a semi conductor chip.

A further object of the present invention is to provide a system for inspecting EUV lithography masks which are capable of measuring mask blanks with a high degree of accuracy and repeatability.

Yet another object of the present invention is to provide a system for inspecting EUV lithography masks which are compatible with conventional mask blank transfer systems and, thus, are operational in standard clean rooms used to manufacture semi conductor chips.

Another object of the present invention is to provide a system for inspecting EUV lithography masks which use an EUV source of radiation that is not hampered by debris migration from the EUV source of radiation.

Yet another object of the present invention is to provide a system for inspecting EUV lithography masks which is capable of identifying defects and assessing the defect for the purpose of repair or discarding of the mask.

Another object of the present invention is to provide a system or inspecting EUV lithography masks that determine printability of the mask in the manufacturing of semi conductor chips.

The invention possesses other objects and advantages especially as concerns particular characteristics and features thereof which will become apparent as the specification continues.

Figure 1:
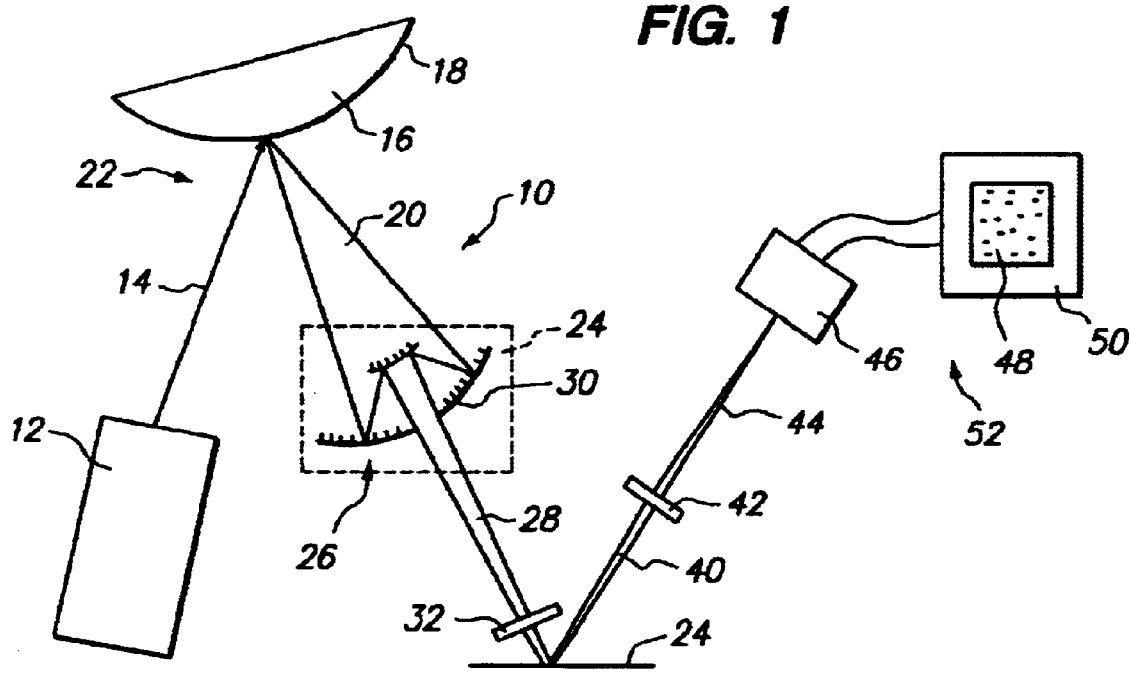
FIG. 1 is a schematic view of the system of the present invention.

For a better understanding of the invention reference is made to the following detailed description of the preferred embodiments thereof which should be taken in conjunction with the prior described drawings.

DETAILED DESCRIPTION OF THE PREFERRED EMBODIMENTS OF THE INVENTION

Various aspects of the present invention will evolve from the following detailed description of the preferred embodiments of the invention, in reference to the hereinabove delineated drawings.

The preferred embodiment of the present invention is denoted in the drawings by reference character 10. System 10 includes as one of its elements a laser source 12 which produces a coherent electromagnetic radiation pulse 14. Laser source 12 is used in the production of extreme ultraviolet radiation (EUV) which will be discussed hereinafter in the present specification. The laser source may take the form of a Nd:YAG Q-switched pulsed laser. Laser produces 300 mJ of frequency-doubled light (532 nm) The pulse duration of the laser 12 may be 8 nanoseconds (ns) with a repetition rate of 10 Hz.

The laser pulse is directed to a target 16 which includes a metallic surface that generates a plasma. For example, the surface 18 of target 16 may take the form of gold, copper, and the like. Contact of the laser pulse 14 with surface 18 of target 16 produces an EUV beam 20 which is essentially continuous in the EUV region between 10 and 16 nm. Thus, laser 12 and target 16 comprise and EUV source 22. The following table 1 indicates an estimate of the photon flux incident on the mask 24 from EUV source 22:

TABLE 1

| | |
|---|---|
| Laser Power (mJ) | 300 |
| Conversion efficiency | 0.20% |
| EUV power at 100 eV in a 1% band width (mJ) | 0.6 |
| N.A. of collection optics | 0.1 |
| EUV power at 100 eV in a 1% band width collected (mJ) | 0.0015 |
| EUV power at 100 eV in a 1% band width collected (in ergs) | 9.38E + 12 |
| No. of 100 eV photons in a 1% band width collected/shot | 9.38E + 10 |
| No. of 100 eV photons in a 1% band width incident on the mask 24 per shot | 2.700E + 10 |

EUV beam 20 passes from EUV source 22, a plasma source, and is condensed or focused by the condenser 24 which may take the form of a Schwarzschild illumination optics 26 (SO). The Schwarzschild system permits control of the collection angle of the exit beam 28 which is intended to impinge on the surface of mask 24. For example, the Schwarzschild optics in the preferred embodiment 10 of FIG. 1 of the present system comprises a 2-mirror multilayer-coated Schwarzschild system. The Schwarzschild system also controls the illumination characteristics of exit beam 28 which are intended to match the illumination of a stepper which is used to manufacture a semiconductor chip (not shown). In addition, the angle of incidence of beam 28 exiting slit 30 of the Schwarzschild system is intended to match the angle of incidence of the stepper, hereinbefore described. Such angle is normally about 5 degrees, although FIG. 1 exaggerates such angle for the sake of clarity. Moreover, the band width of the SO is intended to be 0.36 nm in the preferred embodiment 10. Although the band width of the radiation beam 28 exiting the SO is about 0.13 nm, does not exactly match the band width of a stepper, it has been found that such matching is not required. This condition exists as long as the illumination of exit beam 28 matches the quasi-monochromatic condition of the stepper. The following table also shows the properties of the condenser 26 which are intended to match a stepper projection optics.

TABLE 2

| | |
|---|---|
| Entrance N.A. of the microscope | 0.08 |
| Coherence factor | 0.5 |
| N.A. of the illumination beam | 0.04 |
| Magnification of the source | 2.5 |
| Off-axis collection N.A. of Schwarzschild illumination optics | 0.1 |
| Full-parent N.A. of the Schwarzschild optics | 0.33 |
| Efficiency of the S.O. optics (2 reflections) | 36% |
| Transmission through the slit | 80% |

System 10 is also provided with an aperture plate 32.

Figure 2:
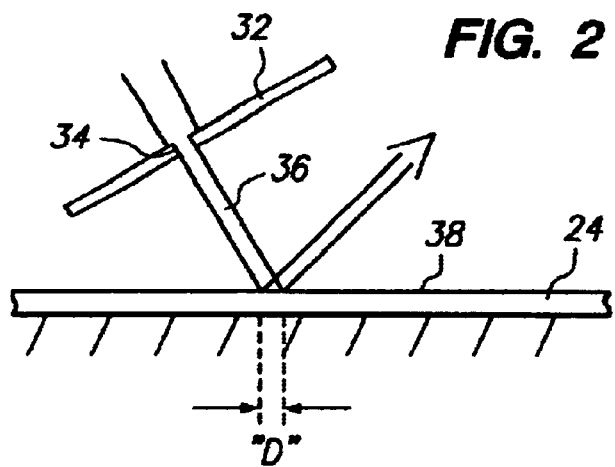
FIG. 2 is a close-up schematic of a detail showing the aperture plate and the area of examination afforded by the system of the present invention.

Aperture plate 32 insures the flaw area of interest on the surface of mask or reticle 24 being inspected by system 10. For example, FIG. 2 shows the aperture 34 of aperture plate to permit a beam 36 to contact surface 38 of mass 24 which has a cross-sectional distance "D", of about 20 nanometers. In essence, beam 36 impinges on an area 20 micrometers by 20 micrometers on surface 38 of mass 24. This small area permits system 10 to inspect masks having patterned and unpatterned surfaces 38 since the area of interest inspected by system 10 is less than any particular patterns on surface 38.

Following reflection of the EUV beam 36 from surface 38 of mask 24, beam 40 passes through zone plate 42, which permits transmission of beam 40 and also resolves the image of the EUV beam 40 reflected from surface 38 of mask 24. The following table represents the properties of zone plate 42.

TABLE 3

| | |
|---|---|
| Wavelength (nm) | 13 |
| Outer zone width Delta (nm) | 81.25 |
| Spectral band | 1% |
| No. of zones (less than delta lambda/lambda) | 100 |
| Focal length ($\mu$m) | 203.125 |
| Lens diameter ($\mu$m) | 32.5 |
| Magnification | 1000 |
| Distance from mask to CCD (mm) | 203.125 |
| F# of the zone plate (F/D) | 6.25 |
| Raylength criterion (nm) | 99.125 |
| Depth of focus ($\mu$m) | 1.016 |

The efficiency and output of zone plate 42 is represented in the following table in the system 10 of the present embodiment:

TABLE 4

| | |
|---|---|
| Efficiency of the zone plate | 20% |
| Transmission of the membrane | 50% |
| No. of 100 eV photons incident on the CCD (full) per shot | 2.700E + 09 |
| # of pixels | |
| X | 1024 |
| Y | 1024 |
| No. of 100 eV photons in a 1% band width incident On the CCD per pixel per shot | 2700 |

Following passage through zone plate 42, beam 44 impinges on detector 46 which provides an image on screen 48 of monitor 50. Detector 46 and monitor 50 represent a charge coupled device (CCD) camera which possess a standard back-thinned, back illuminated 1024×1024 pixel rating. CCD camera 52 is also highly efficient since long integration times are not required due to the quick measurement rate of system 10 on mask 38. Any defects on surface 38 of mask 24 will produce dark spots on screen 48 or variations in intensity.

Figure 3:
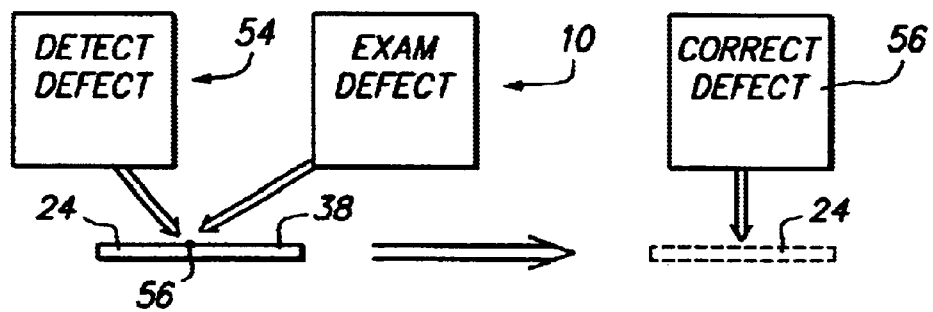
FIG. 3 is a block diagram depicting the general process used in the preparation of a lithography mask employing the system of the present invention.

System 10 of the present invention as depicted in use schematically on, FIG. 3 in which a defect detector 54 is used of generally conventional configuration. Once defect 56 is found system 10 of the present invention may be used to examine the defect using the parameters of the EUV stepper device (not shown) normally employed to manufacture a semi-conductor chip from mask 24. Device 10 assesses the severity of the defects in terms of reflectivity losses and printability of the defects on the mask 24. A subsequent system 56 may be employed to repair the masks if possible for use in the construction of a semi-conductor chip. Of course, a fiducial mark detection system, known in the art, may be employed with defect detector 54, and the inspection system 10 of the present invention in order to locate the aerial image on the surface 38 of mask 24 for production of images on screen 48 of monitor 50 of the CCD camera.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A system for inspecting a EUV lithography mask, comprising:
    a. a laser source producing a coherent electromagnetic radiation pulse;
    b. target means for receiving said pulse and producing EUV beam of a certain intensity;
    c. focusing means for condensing said EUV beam;
    d. an aperture plate for defining the cross sectional area of said condensed EUV beam for impingement on and reflection from the lithography mask;
    e. a transmission zone plate for collecting and resolving an image of the EUV beam reflected from the lithography mask; and
    f. a detector for receiving said EUV passed through said zone plate and producing an aerial image of the mask.

2. The system of claim 1 in which said laser source comprises a target producing a plasma when reacting with said coherent electromagnetic radiation pulse.

3. The system of claim 2 in which said target includes a metallic surface selected from the group essentially consisting of gold and copper.

4. The system of claim 1 in which said means for condensing said EUV beam comprises a Schwarzschild optic.

5. The system of claim 4 in which said Schwarzschild optic produced a condensed EUV beam which imprints the mask at selected angle of incidence.

6. The system of claim 1 which additionally comprises clean room means for containing said laser source, said target means, said focusing means, said aperture plate and said transmission zone plate.

7. The system of claim 6 in which said laser source comprises a target producing a plasma when reacting with said coherent electromagnetic radiation pulse.

8. The system of claim 7 in which said target includes a metallic surface selected from the group essentially consisting of gold and copper.

9. The system of claim 6 in which said means for condensing said EUV beam comprises a Schwarzschild optic.

10. The system of claim 9 in which said Schwarzschild optic produced a condensed EUV beam which imprints the mask at selected angle of incidence.

\* \* \* \* \*